United States Patent [19]

Ellison et al.

[11] Patent Number: Plant 6,622

[45] Date of Patent: Feb. 21, 1989

[54] ASPARAGUS PLANT NAMED LINDA

[75] Inventors: J. Howard Ellison, Milltown; John J. Kinelski, Princeton, both of N.J.

[73] Assignee: Rutgers University, New Brunswick, N.J.

[21] Appl. No.: 77,521

[22] Filed: Jul. 6, 1987

[51] Int. Cl.[4] ..... A01H 5/00

[52] U.S. Cl. ..... Plt./89

[58] Field of Search ..... Plt./89

*Primary Examiner*—Robert E. Bagwill

*Attorney, Agent, or Firm*—Frank B. Robb

[57] ABSTRACT

A female asparagus plant having rust and Fusarium resistance, vigorous in growth, high quality spear production, all characteristics being transmitted to progeny.

1 Drawing Sheet

1

This invention relates to asparagus plants and is particularly directed to a female variety which we have denominated as "Linda" and also identified as our No. 277C, which variety is one of many produced in a very extensive and intensive program of development carried on in New Jersey and the result of long periods of trial and crossing of many varieties, some of which were improvements and others obviously not worth considering further.

In our program of hybridization, we have discovered a large number of plants, many of them found in fields of the Mary Washington variety but well known and widely grown in various areas, the particular area to which we refer being south New Jersey where many fields are infested with Fusarium and have rust problems of extensive nature.

The obvious desirability of providing asparagus varieties which resist diseases and rust is clear and in fact our new variety "Linda" does resist rust and is tolerant to Fusarium is a very vigorous plant and produces high yields of very high quality spears, the ultimate desirable result for any grower and for growth of asparagus on a commercial basis.

Figure 1:
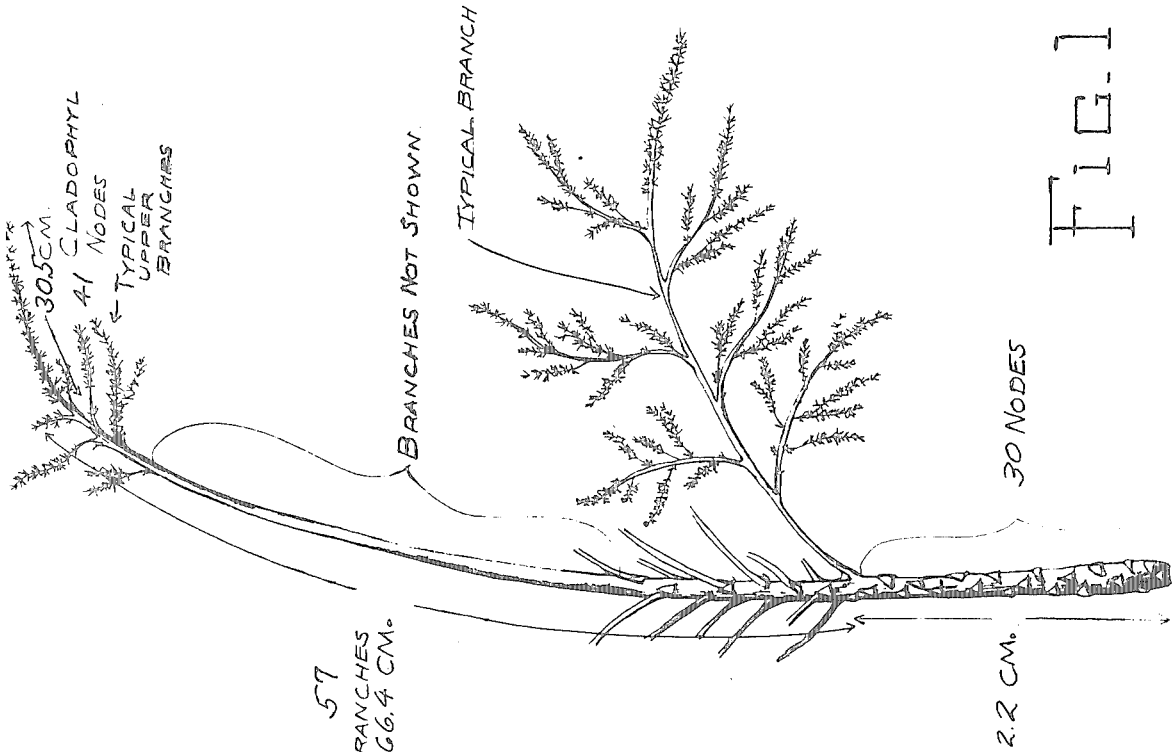

Exemplary of some of the improvements provided by the instant plant which we have asexually reproduced by crown division and tissue culture, are data illustrated in a drawing appended hereto wherein FIG. 1 is of a typical stalk of a plant for illustration of dimensions and various aspects, to distinguish and provide a basis in our program of comparison.

Figure 2:
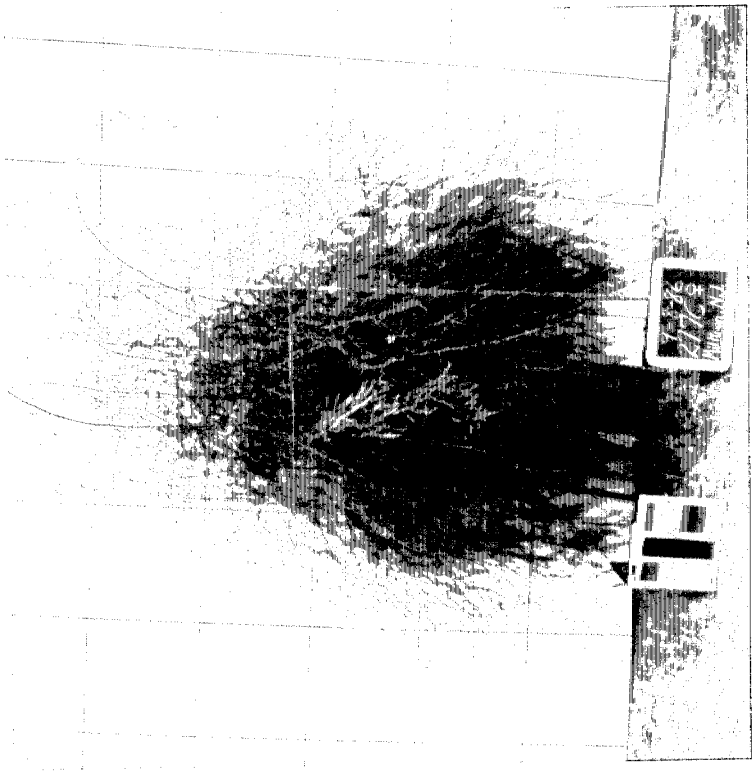

FIG. 2 is a color illustration which is of a typical plant, as it has gone to seed in the fall so as to illustrate its general overall appearance, the color obviously being determined by the ability to reproduce the same in a color disclosure of this kind and comparisons of the color notations referred to the Munsell Limit Color Cascade.

In addition to the foregoing, we have provided a summary of certain plant data, much of the data being applied to the stalk for example shown in FIG. 1 and illustrative of the various dimensional aspects where possible to define the same, so as to illustrate the differences which may exist between the plant of the instant variety and others in the programs which we have been carrying on.

2

Certain of the data are translated onto the drawing in particular areas and summarized as noted in the data summary which follows here.

| ASPARAGUS PLANT DATA | |
|---|---|
| Stalk Data | |
| Number of nodes below first branch | 30 |
| Number of cm from crown to first branch | 62.2 |
| Number of branches | 57 |
| Number cm between first and last branch | 166.4 |
| Internode length in cm between branches | 2.92 |
| Number of cladophyll nodes beyond last branch | 41 |
| Number of cm beyond last branch | 30.5 |
| Internode length in cm beyond last branch | 0.74 |
| Note: All above are largest stalk | |
| Largest stalk diameter in mm | 25.6 |
| Mean diameter of three largest stalks in mm | 24.3 |
| Number of stalks | 16 |
| Stalk vigor index | 9.448 |
| Mature stalk color, bloom removed. Color No. (1) | 21-15 |
| Crown to first branch of highest headed stalk | 83.2 cm |
| Flower Data | |
| Petal tip (yellow) Color No. (1) | 25-3 |
| Petal base (green) Color No. (1) | 23-10.5 |
| Flower length (mm) | 4.6 |
| Flower width at midpoint (mm) | 2.6 |
| Fruit Data (277c × 22-8) | |
| Weight of 100 fruit (g) | 28.1 |
| Water displacement of 100 fruit (ml) | 29.0 |
| Number of seed per 100 fruit | 274 |
| Weight of seed per 100 fruit (g) | 11.2 |
| Mean weight per seed | 0.0409 |
| Water displacement of seed of 100 fruit (ml) | 13.0 |
| Mature fruit Color No. (1) | 33-12 |
| Cladophyll Data | |
| Number per node | 2.83 |
| Length (mm) | 23.6 |
| Width (mm) | 0.144 |

It should be noted that our new variety, is one of the parent plants of another variety which we have found is a desirable one to reproduce and offer to commerce, transmitting to the produced hybrid which we have designated "Jersey Knight" many if not all of the most desirable characteristics and is the subject of separate disclosure and application for patent.

We claim:

1. A new and distinct variety of asparagus plant as herein shown and described, characterized particularly as to novelty by the unique combination in a female variety, of good tolerance to Fusarium and rust, together with vigorous plant growth and high yields of high quality spears, such characteristics being transmitted to progeny.

* * * * *